United States Patent
Matsui

(10) Patent No.: US 7,952,701 B2
(45) Date of Patent: May 31, 2011

(54) SURFACE INSPECTION METHOD AND INSPECTING DEVICE USING THE SAME

(75) Inventor: Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 289 days.

(21) Appl. No.: 12/367,673

(22) Filed: Feb. 9, 2009

(65) Prior Publication Data

US 2009/0213364 A1    Aug. 27, 2009

(30) Foreign Application Priority Data

Feb. 27, 2008   (JP) .................................. 2008-045737

(51) Int. Cl.
   *G01N 21/00*    (2006.01)
(52) U.S. Cl. ................. 356/237.3; 356/237.1; 356/237.4
(58) Field of Classification Search .... 356/237.1–241.6, 356/242.1–243.8, 426–431, 600–640
   See application file for complete search history.

(56) References Cited

U.S. PATENT DOCUMENTS

| | | | | |
|---|---|---|---|---|
| 5,726,748 A | * | 3/1998 | Morris | 356/237.2 |
| 5,798,829 A | * | 8/1998 | Vaez-Iravani | 356/237.1 |
| 6,271,916 B1 | * | 8/2001 | Marxer et al. | 356/237.3 |
| 7,359,045 B2 | * | 4/2008 | Some | 356/237.5 |
| 7,602,482 B2 | * | 10/2009 | Matsui | 356/237.3 |
| 2001/0015802 A1 | * | 8/2001 | Tomita et al. | 356/237.2 |
| 2007/0268484 A1 | | 11/2007 | Matsui | |

FOREIGN PATENT DOCUMENTS

| | | |
|---|---|---|
| JP | 62-153737 | 7/1987 |
| JP | 2001-255578 | 9/2001 |
| JP | 2007-309713 | 11/2007 |

OTHER PUBLICATIONS

U.S. Appl. No. 12/207,536, filed Sep. 10, 2008, Matsui.

* cited by examiner

*Primary Examiner* — Gregory J Toatley
*Assistant Examiner* — Jarreas C Underwood
(74) *Attorney, Agent, or Firm* — McDermott Will & Emery LLP

(57) ABSTRACT

If an illuminance of a measurement spot is limited in order to prevent heat damage on an article to be inspected, since detection sensitivity and a detection speed are in a relation of trade-off, it is difficult to improve one of them without sacrificing the other or to improve both of them. Also, there is a problem that the detection sensitivity is lowered on an outer circumference portion than on an inner circumference portion of the article to be inspected.

A plurality of measurement units comprising an illumination optics, a measurement spot, a collection optics, and a light detection optics are provided, inspection results obtained from the plurality of measurement spots are integrated, and light-amount distribution to each measurement spot is controlled according to a scan radial position.

27 Claims, 10 Drawing Sheets

Secondary scan direction

SURFACE INSPECTION METHOD AND INSPECTING DEVICE USING THE SAME

BACKGROUND OF THE INVENTION

1. Field of the Invention

The present invention relates to an art to detect fine contaminant particles/defects on a thin film substrate, a semiconductor substrate, a photomask and the like, if present. The present invention relates particularly to an art to improve detection sensitivity of the fine contaminant particles/defects.

2. Background Art

In a production line of the semiconductor substrate, thin film substrate and the like, inspection of a contaminant particle adhering to the surface of the semiconductor substrate, thin film substrate and the like is conducted in order to monitor dusting situation of a manufacturing device. For example, in the case of the semiconductor substrate before a circuit pattern is formed, a fine contaminant particle or defect with a size of several tens nm or less should be detected on the surface. As an art to detect the fine defects on the surface of an article to be inspected such as a semiconductor substrate and the like, as described in U.S. Pat. No. 5,798,829, for example, there is a prior art in which a focused laser light flux is fixedly irradiated onto the semiconductor substrate surface (an irradiated region formed by the irradiated laser light flux on the semiconductor substrate surface at this time is referred to as an illumination spot), a scattered light from the contaminant particle generated when the contaminant particle adhere onto the semiconductor substrate is detected, and the contaminant particle or defect on the entire surface of the semiconductor substrate are inspected by rotation and translational feeding of the semiconductor substrate. An ellipsoidal mirror is used for detection of the scattered light, and by setting a detection position on the semiconductor substrate at a primary ellipsoidal focal point and arranging a photosensitive surface of a photosensitive element at a secondary focal point, the scattered light generated in the contaminant particle can be focused with a wide solid angle so that the fine contaminant particle can be detected. As the laser light flux in plural for illuminating the semiconductor substrate in this prior art, only one flux corresponds to a single incident angle, and there is only one illumination spot formed on the semiconductor substrate surface by the laser light flux.

As another prior art, as described in JP Patent Publication (Kokai) No. 2001-255578, for example, condenser lenses and photodetectors are arranged at positions where a plurality of elevation angles and a plurality of azimuthal angles are combined with respect to the semiconductor substrate surface, and by detecting the scattered light focused by each of the condenser lenses by the photodetectors, detection in an advantageous direction is made possible according to a three-dimensional radiation distribution characteristics of the scattered light from the fine contaminant particle. In this prior art, too, two laser light fluxes of oblique illumination and normal illumination are provided for illuminating the semiconductor substrate, but there is only one laser light flux which corresponds to a single incident angle, and there is only one illumination spot formed by the laser light flux on the semiconductor substrate surface.

SUMMARY OF THE INVENTION

In the semiconductor substrate (semiconductor wafers), thin film substrates, photomasks and the like, a size of the contaminant particle or defect requiring detection is rapidly reducing with increase in density. A scattering light signal amount S obtained when scattered light from a contaminant particle is detected by a photodetector when a contaminant particle on the surface of an article to be inspected having a flat and smooth surface is detected is in proportion to a value of the right-hand side in the following formula in general, if a particle diameter of the contaminant particle is small to an extent that follows Rayleigh scattering.

S∝illuminance of illumination light×particle diameter of contaminant particle to the $6^{th}$ power×illumination wavelength to the $-4^{th}$ power×collection efficiency of scattered light detection optics×duration of scattered light×quantum efficiency of photodetector×gain of photodetector A size of noise N at this detection is substantially in proportion to the value of the right-hand side in the following formula in general.

N∝square root of (illuminance of illumination light×area of illumination spot×scattering power on the surface of an article to be inspected)

Thus, as factors serving to raise detection sensitivity of the contaminant particle or defect, the following are known:

(1) Illuminance of the illumination light in the illumination spot is increased so that strong scattered light can be obtained;

(2) A wavelength of the illumination light is reduced so that strong scattered light can be obtained;

(3) The numerical aperture of a collection optics is increased so that the scattered light can be focused with efficiency;

(4) Performances of the photodetector such as quantum efficiency and signal-to-noise ratio are improved;

(5) An area of the illumination spot is reduced so as to decrease background scattering light;

(6) A primary scan speed of a stage for moving a non-inspected article is reduced so as to prolong time during which the contaminant particle or defect passes through the illumination spot; and (7) A diameter of the illumination spot in a primary scan direction is increased so as to prolong time during which the contaminant particle or defect passes through the illumination spot.

However, even if they are employed, the sensitivity improvement is not easy at present due to the following reasons:

(1) If the illuminance of the illumination spot is increased, a temperature on the surface of the article to be inspected is raised by absorbing energy of the illumination light, and risk that the article to be inspected is subjected to damage by heat becomes high. Therefore, there is an upper limit on the increase in the illuminance of the illumination spot, and the illuminance can be increased only within the range.

(2) A wavelength of a light source available as a light source having a suitable output and the like for detection of the contaminant particle or defect is limited, and the reduction in the wavelength has a limitation.

(3) A collection efficiency of the scattered light emitted from the contaminant particles or defects does not exceed 100%. The efficiency is approximately 50% in general with the prior arts, and it is already impossible to double the efficiency in the future.

(4) The quantum efficiency and signal-to-noise ratio of a photomultiplier tube having been used as a photodetector suitable for detection of weak scattering light are already close to a theoretical limit and marked improvement can not be expected in the future.

(5) It is effective to reduce the area of the illumination spot but there is a problem that time required for inspection of the entire surface of the article to be inspected becomes long at the same time.

(6) To reduce the primary scan speed has a problem that time required for inspection of the entire surface of the article to be inspected becomes long similarly to (5).

(7) Only by increasing the diameter of the illumination spot in the primary scan direction does not have an effect since it is offset by increase in the background scattering light caused by increase in the area of the illumination spot at the same time, and if the diameter of the illumination spot in a direction orthogonal to the primary scan direction is reduced in order that the area of the illumination spot is not increased, there is a problem that time required for inspection of the entire surface of the article to be inspected becomes long similarly to (5).

Then, in view of the above circumstances, problems of the present invention is to improve the detection sensitivity of the contaminant particles or defects without sacrificing time required for inspection of the entire surface of the article to be inspected while damage on the article to be inspected by heat is kept within an allowable range or to the contrary, to improve time required for inspection of the entire surface of the article to be inspected without sacrificing the detection sensitivity of the contaminant particles or defects. An object of the present invention is to provide an art that can solve the problems.

A surface inspection apparatus to be described herein comprises a stage for moving an article to be inspected which moves/scans the article to be inspected with linear velocities different between an inner circumference portion and an outer circumference portion by combination of primary scan of rotational movement and secondary scan of translational movement, a light source for illumination, illuminating means for forming an illumination spot by irradiating light from the light source for illumination to a predetermined position on the surface of the article to be inspected, and scattering/diffraction/reflection light detection means for detecting light scattered/diffracted/reflected from the illumination spot for detecting a contaminant particle or defect present on the surface or inside the vicinity of the surface of the article to be inspected by the detection result.

In order to solve the above problems, the present invention comprises:

(1) a plurality of measurement units including an illumination optics for forming an illumination spot by irradiating an illumination light flux to a predetermined position on the surface of an article to be inspected, a collection optics for collecting light scattered/diffracted/reflected from the illumination spot, and a light detection optics for detecting the scattered/diffracted/reflected light collected by the collection optics and converting it to an electric signal, (2) the plurality of measurement units are configured so that they are arranged substantially along a secondary scan direction of the stage for moving the article to be inspected, and in more detail, the plurality of measurement units are configured such that (3) at least one illumination spot in the plurality of illumination spots irradiated by the plurality of measurement units is moved on the surface of the article to be inspected toward an inner circumference portion during the secondary scan, and another at least one illumination spot is moved toward an outer circumference portion. Moreover, the plurality of measurement units are configured such that (4) the plurality of measurement units can illuminate the surface of the article to be inspected with different illuminances and in more detail, (5) the illuminance of each illumination spot of the plurality of measurement units can be changed during the secondary scan. In more detail, the illuminance of the illumination spot is made higher in inspection of the outer circumference portion than that in the inspection of the inner circumference portion. That is because a decrease of "duration of generated light" in the "net signal amount" is compensated by increase in the illuminance since the scattered/diffracted/reflected light from the contaminant particle or defect is in proportion to the illuminance of the illumination spot as mentioned above. On the other hand, an effect that a temperature of the article to be inspected or particularly a temperature in the vicinity of its surface is raised by heat energy generated by the irradiated laser light is, supposing that the illuminance of the irradiated laser light is constant, if the laser light is irradiated to the article to be inspected which is not still but is moving, as described in Laser Process Art Handbook, pp. 224-230, such that a rising temperature becomes small as the moving linear velocity of the article to be inspected is increased. That means to the contrary that the larger the moving linear velocity is, the larger laser illuminance is allowed, supposing that a temperature allowing the rise is constant.

Then, in the present invention, (6) the illuminance of each illumination spot of the plurality of measurement units is changed corresponding to a radial position of each illumination spot on the surface of the article to be inspected so that the illuminance becomes low as the position goes toward the inner circumference portion on the surface of the article to be inspected, while it becomes high toward the outer circumference portion.

And for at least two or more of the plurality of measurement units, in the present invention, (7) the measurement units are arranged so that inspection regions to be filled by traces drawn by the illumination spot on the surface of the article to be inspected with the primary scan rotation and secondary scan movement of the stage for moving the article to be inspected substantially overlap each other, and an inspection result of the overlapped inspection regions solve the above problems by obtaining the inspection results of each of the measurement units in integration.

Also, in the present invention, at least one or more of the plurality of measurement units also includes an art in which (8) a collection optics for collecting the scattered/diffracted/reflected light from the illumination spot by two or more plural azimuthal directions and a light detection optics made of a plurality of photodetectors for individually detecting the scattered/diffracted/reflected light focused by the plurality of azimuthal directions and converting it to an electric signal or one photodetector having a plurality of photosensitive pixels are provided and particularly the measurement unit in which the inspection regions are substantially overlapped includes an art in which (9) one of the measurement unit pair whose inspection regions are substantially overlapped with each other is provided with the collection optics for mainly collecting forward scattering light and backward scattering light individually in the light scattered from the illumination spot and a light detection optics including two photodetectors for individually detecting the focused forward scattering light and backward scattering light and converting them to electric signals or one photodetector having two photosensitive pixels, while the other measurement unit is provided with the collection optics for mainly collecting right side-scattering light and left side-scattering light individually in the light scattered from the illumination spot and a light detection optics including two photodetectors for individually detecting the focused right side-scattering light and left side-scattering light and converting them to electric signals or one photodetector having two photosensitive pixels.

Moreover, in the configuration of the surface inspection apparatus according to the present invention, in order to divide the light from the illumination light source and give it to the plurality of measurement units,

(10) an illumination light-flux dividing optics for dividing the light flux emitted from the light source for illumination into plural is provided. More specifically, the illumination light flux dividing optics includes an art in which

(11) a mechanism for changing illuminance for illuminating the surface of the article to be inspected is made as a mechanism for changing an intensity ratio of two light fluxes separated by a polarization separation element by combining the polarization separation element such as a polarization beam splitter, a Wollaston prism and the like and a half-wave plate and by changing a direction of a slow axis of the half-wave plate with respect to a polarization azimuth of the polarization element through rotation.

According to the present invention, improvement of inspection signal-to-noise or improvement of inspection throughput, improvement in a detection sensitivity difference of contaminant particles/defects between an inner circumference portion and an outer circumference portion of a semiconductor wafer, and effective use of an output of a laser light source for illumination on board can be satisfied at the same time. The present invention will be described below in more detail referring to an embodiment.

Figure 1:
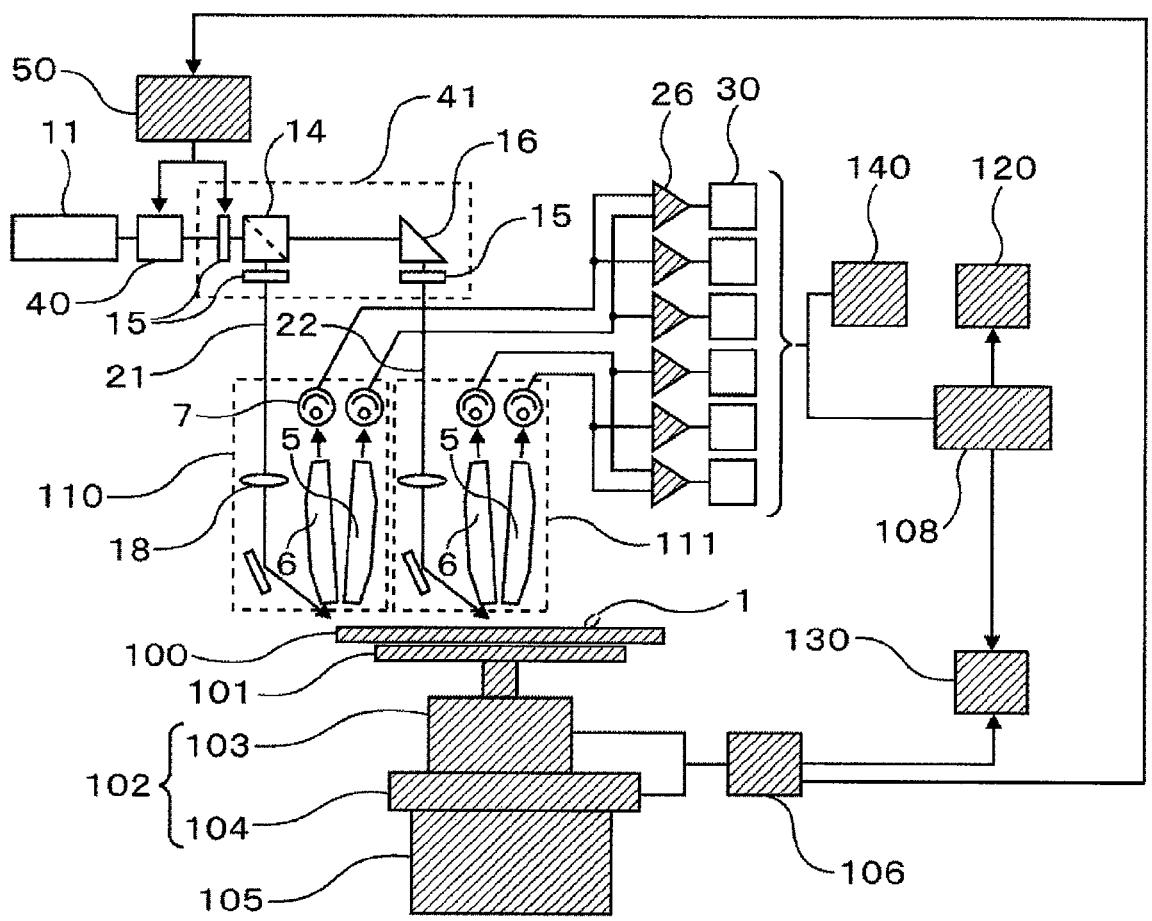
FIG. 1 is a diagram illustrating configuration of a first embodiment of a surface inspection apparatus according to the present invention.

DESCRIPTION OF SYMBOLS 1 contaminant particle
2 movement trace of contaminant particle
3 illumination spot
5, 6 collecting concave mirror group
7 photodetector
11 illumination laser light source
14 polarization beam splitter
15 half-wave plate
16 folding mirror
18 irradiation lens
21, 22 illumination light flux
26 amplifier
30 Analog-to-digital converter
40 light-amount adjustment mechanism
41 illumination light-flux dividing optics
42 illumination optics
43 collection optics
50 illuminance control portion
100 semiconductor wafer
101 chuck
102 stage for moving an article to be inspected
103 rotation stage
104 translation stage
105 Z-stage
106 inspection coordinate detection mechanism
108 contaminant particle/defect determination mechanism
110 first measurement unit
111 second measurement unit
120 particle diameter calculation mechanism
130 contaminant particle/defect coordinate detection mechanism
140 contaminant particle/defect classification mechanism
161 collecting paraboloid mirror
162 focal point of collecting paraboloid mirror 161
163 imaging paraboloid mirror
164 focal point of imaging paraboloid mirror 163
165 common optical axis
166 parallel light flux
167 normal of semiconductor wafer 100 surface
168 inclination angle of paraboloid mirror optical axis

DETAILED DESCRIPTION OF THE PREFERRED EMBODIMENTS

An embodiment of the present invention will be described below in detail using the attached drawings.

First Embodiment

Figure 2:
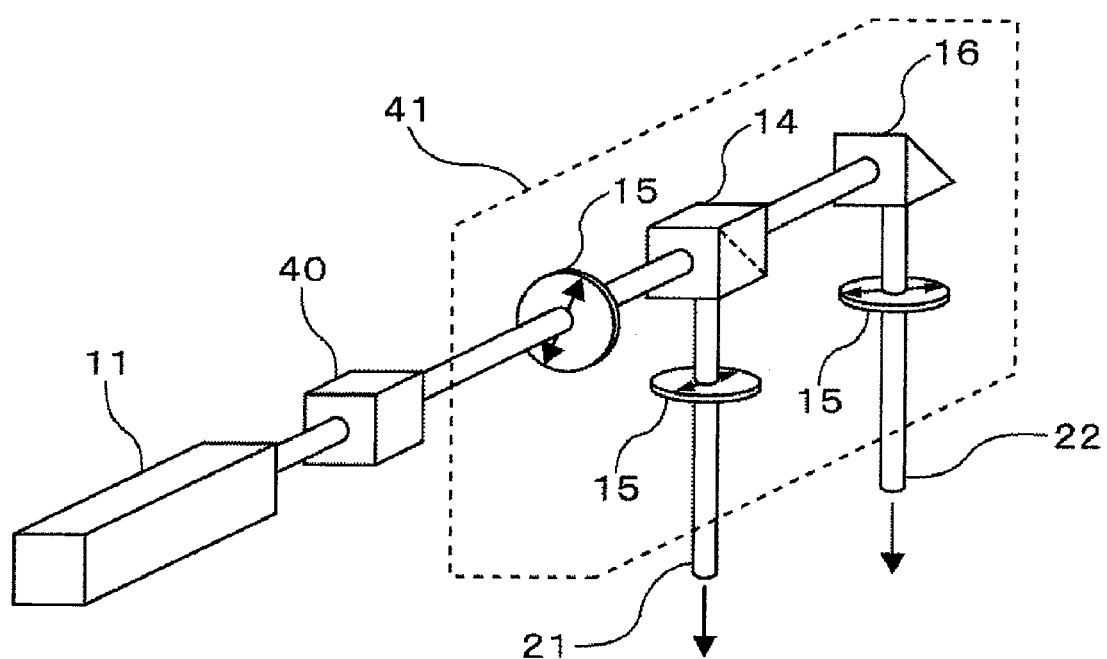
FIG. 2 is a diagram illustrating configuration of an illumination light-flux dividing optics.
Figure 3:
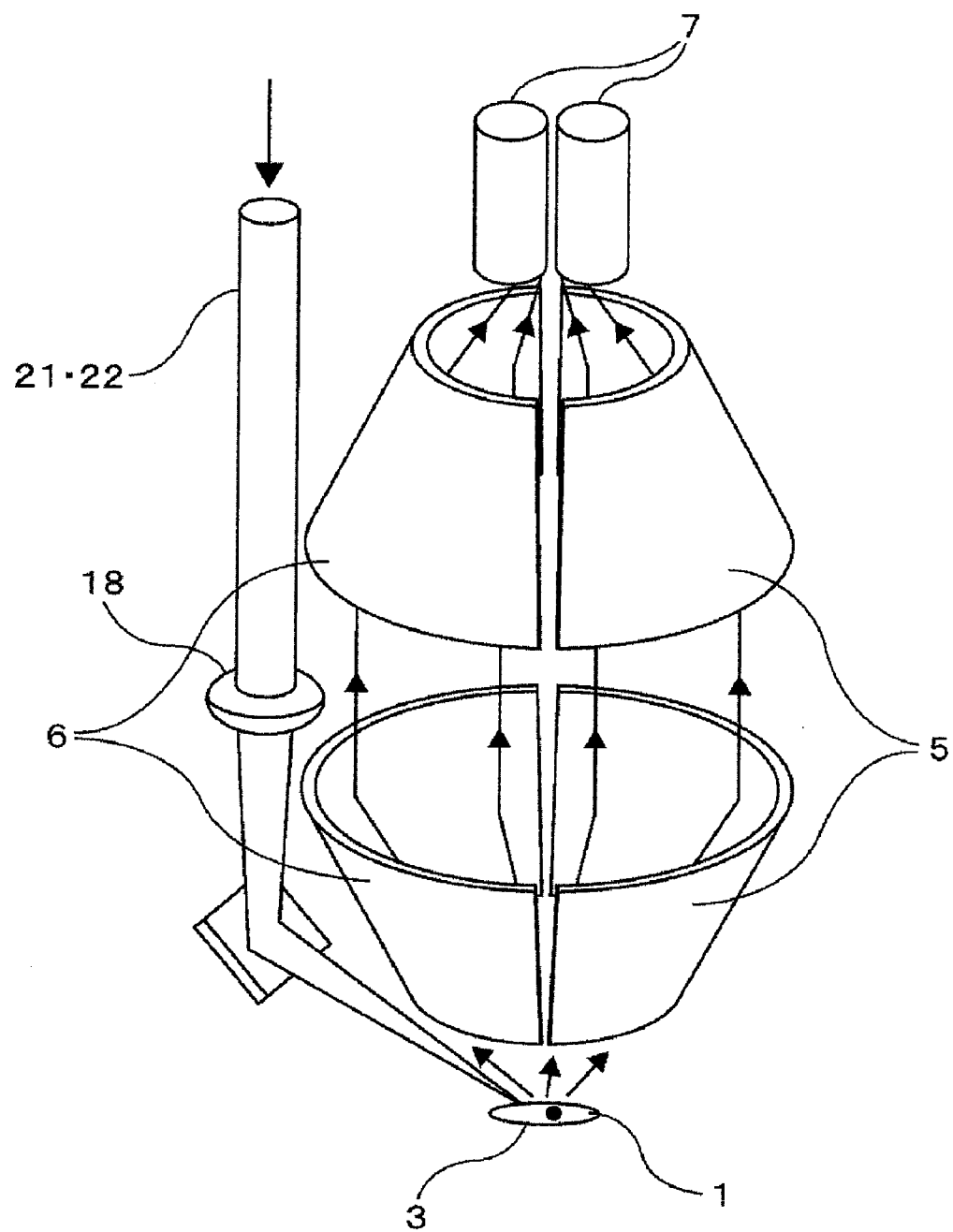
FIG. 3 is a diagram illustrating configuration of a measurement unit.
Figure 4:
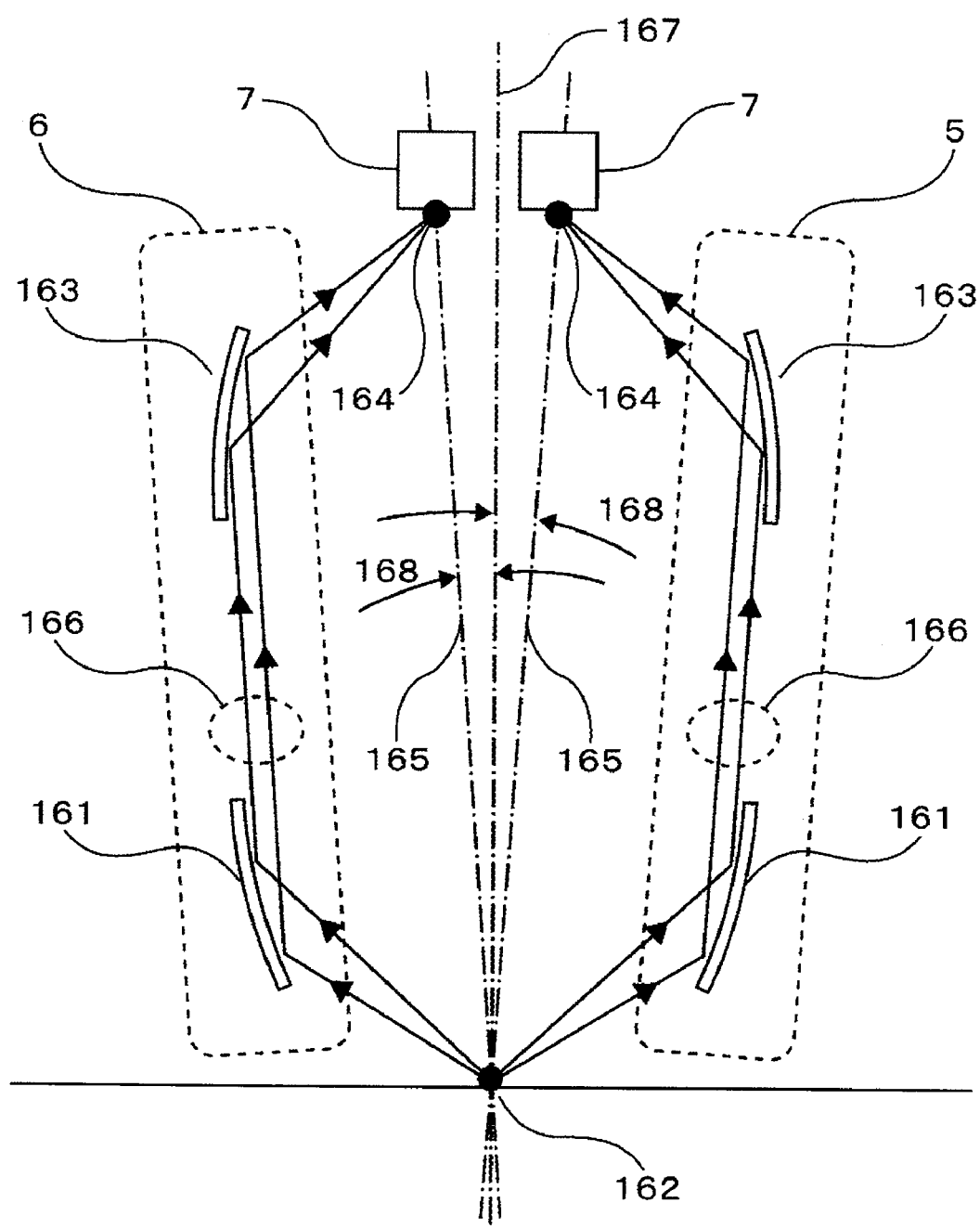
FIG. 4 is a diagram illustrating configuration of a collecting concave mirror group.

A first embodiment of a contaminant particle/defect inspecting device using a contaminant particle/defect inspection method of the present invention is shown in FIG. 1. A semiconductor wafer 100, which is an article to be inspected, is vacuum-adsorbed by a chuck 101, and this chuck 101 is mounted on a stage 102 for moving an article to be inspected made of a rotation stage 103 and a translation stage 104, and a Z-stage 105. Above the semiconductor wafer 100, an illumination light source 11, a light-amount adjustment mechanism 40, an illumination light-flux dividing optics 41, a first measurement unit 110, and a second measurement unit 111 are arranged. For the illumination light source 11, a laser light source is used. A laser beam emitted from the light source 11 has its light amount adjusted by the light-amount adjustment mechanism 40 and then, enters the illumination light-flux dividing optics 41, where the beam is divided into two illumination light fluxes 21, 22 constituting a predetermined intensity ratio and then, is introduced to the two measurement units 110, 111. In this embodiment, as the illumination light-flux dividing optics 41, an optics in which a polarization beam splitter 14 and a half-wave plate 15 are combined as shown in FIG. 2 is used, and by changing a direction of a slow axis of the half-wave plate through rotation with respect to a polarization azimuth of the polarization beam splitter 14, the intensity ratio of the illumination light fluxes 21, 22 can be changed. Also, each of the illumination light fluxes 21, 22 have an equal polarization state. Here, instead of the polarization beam splitter 14, a polarization separation element such as a Wollaston prism and the like can be used. Each of the measurement units 110, 111 has, as shown in FIG. 3, an illumination optics 42 for forming an illumination spot 3 by irradiating an illumination light flux to a predetermined position on the semiconductor wafer 100 surface, a collection optics 43 for collecting light scattered/diffracted/reflected form the illumination spot 3, and a photodetector 7 for detecting the scattered/diffracted/reflected light collected by the collection optics and converting it to an electric signal. It is so configured that the illumination light fluxes 21, 22 guided by each of the measurement units 110, 111 enter an irradiation lens 18 and obliquely enter the surface of the semiconductor wafer 100 as an article to be inspected substantially at a Brewster angle to crystalline silicon Si. As mentioned above, the illumination light fluxes 21, 22 have an equal polarization state and each illumination spot 3 of the two measurement units 110, 111 is illuminated in an equal polarization state (such as P-polarization together, for example). Collecting concave mirror groups 5, 6 are configured so that a scattered light can be collected at a low elevation angle so that a scattered light of a fine contaminant particle that follows Rayleigh scattering can be efficiently captured and that a collecting concave mirror group 5 mainly captures a forward scattering light, while a collecting concave mirror group 6 mainly captures a backward scattering light in relation to an oblique incidence illumination light onto the surface of the article to be inspected. Details of the collecting concave mirror groups 5, 6 are shown in FIG. 4. The collecting concave mirror groups 5, 6 are constituted by combining two concave mirrors in a structure in which a part of an ellipsoidal mirror is cut out, and optical axes of the two concave mirrors are mounted with inclination to a normal of the semiconductor wafer 100 surface. If a contaminant particle 1 passes through the illumination spot 3, a forward scattering light component in the scattered light generated at the contaminant particle 1 is mainly captured by the collecting concave mirror group 5, and converted to a light scattering light signal by one of the photodetectors 7. Also, a backward scattering light component is mainly captured by the collecting concave mirror group 6 and converted to the light scattering light signal by the other photodetector 7. In this embodiment, a photomultiplier tube is used as the photodetector 7, but a photodetector of other detection principles may be used as long as the scattered light from the contaminant particle can be detected with a high sensitivity. The first measurement unit 110 and the second measurement unit 111 are arranged so that measurement spots provided by each of them pass through the rotation center of the rotation stage 103 and are located side by side on a straight line in parallel with a moving direction of the translation stage 104. An interval between the two measurement units is set so that an interval between the measurement spots provided by each of them is equal to the maximum inspection radius corresponding to an outermost circumference when the semiconductor wafer 100 is secondary-scanned by the translation stage 104 in inspection. That is, when the measurement spot of the first measurement unit 110 (hereinafter referred to as a "first illumination spot") is located at the center of the semiconductor wafer 100, a measurement spot of the second measurement unit 111 (hereinafter referred to as a "second illumination spot") is on a circumference of the maximum inspection radius position. The maximum inspection radius is set slightly smaller than a radius of the semiconductor wafer 100 so that when the illumination spot contacts an outer circumferential edge of the semiconductor wafer 100, extremely intense reflection, diffraction or scattering light, if generated, will not damage the photodetector 7. Instead of setting the interval between the measurement spots of the two measurement units equal to the maximum inspection radius as in this embodiment, the interval may be set substantially according to the radius of the semiconductor wafer 100, and the illuminance of the illumination spot may be controlled to be reduced or shut off if there is a possibility that one of the measurement spots contacts the outer circumferential edge of the semiconductor wafer 100. With this configuration, along with the secondary scan of the translation stage 104, the first measurement spot is moved on the semiconductor wafer 100 surface toward the outer circumference from the center of the semiconductor wafer 100, while the second measurement spot is, on the contrary, moved toward the center from the outer circumference of the semiconductor wafer 100. Six output signals in total obtained by adding a sum output signal of the two photodetectors 7 of the first measurement unit 110 and a sum output signal of the two photodetectors 7 of the second measurement unit 111 to each output signal of the four photodetectors 7 in total of the two measurement units 110, 111 are individually processed. That is, each output signal is individually amplified by six amplifiers 26 and then, sampled by similarly six analog-to-digital converters 30 per predetermined sampling interval $\Delta T$ and converted to digital data. The digital data is compared with a predetermined detection threshold value by a contaminant particle/defect determination mechanism 108, and if the digital data is more than the threshold value, the contaminant particle/defect determination mechanism 108 determines that the digital data is caused by a contaminant particle/defect and creates contaminant particle/defect determination information. A contaminant particle/defect coordinate detection mechanism 130 calculates a coordinate position of the detected contaminant particle/defect when the contaminant particle/defect determination information is created. At this time, if the contaminant particle/defect is detected in the digital data deriving from the first measurement unit 110, a coordinate position corresponding to the position of the first measurement spot is calculated, and if the contaminant particle/defect is detected in the digital data deriving from the second measurement unit 111, a coordinate position corresponding to the position of the second measurement spot is calculated. When the coordinate position of the detected contaminant particle/defect is acquired, subsequently, a particle diameter calculation mechanism 120 calculates a size of the detected contaminant particle/defect from the digital data corresponding to the contaminant particle/defect. However, if the illuminance of each illumination spot 3 is changed by changing the setting of the illumination light-flux dividing optics 41, the scattered light illuminance is changed corresponding to the change (in proportion) even in the same contaminant particle, and the calculation of the size is made after the value of the digital data is corrected according to the illuminance change of each illumination spot 3. Also for the detected contaminant particle/defect, on the basis of a ratio between the output signal from the photodetector mainly detecting the forward scattering and the output signal from the photodetector mainly detecting the backward scattering, type determination of the contaminant particle/defect is made. Moreover, in this embodiment, by means of the secondary scan with the translation stage 104 only for a stroke corresponding to the maximum inspection radius, each measurement spot of the both two measurement units can scan substantially the entire region from the center of the semiconductor wafer 100 to the outer circumference corresponding to the maximum inspection radius, the each point within this region on the semiconductor wafer 100 surface is scanned by the both measurement spots without fail. From this fact, in this embodiment, a function for detecting the contaminant particle/defect by integrating the digital data deriving from the first measurement unit 110 and the digital data deriving from the second measurement unit 111 corresponding to the same coordinate position on the semiconductor wafer 100 surface is provided. It is needless to say that the detection signal-to-noise ratio is improved by this processing. Specifically, by adding the digital data from the both measurement units corresponding to the same coordinate for use, improvement of the detection signal-to-noise ratio by √2 times on an average can be expected as compared with the case where only the digital data from a single measurement unit is used. Also, by means of the secondary scan with the translation stage 104 only for the stroke corresponding to ½ of the maximum inspection radius in this embodiment, the first measurement spot can scan an area of ½ of substantially the entire region from the center of the semiconductor wafer 100 to the circumference corresponding to ½ of the maximum inspection radius, while the second measurement spot can scan the area of ½ of substantially the entire region from the outer circumference corresponding to the maximum inspection radius of the semiconductor wafer 100 to the circumference corresponding to ½ of the maximum inspection radius, and each point in this region on the semiconductor wafer 100 surface is scanned by either of the measurement spots without fail. From this fact, in this embodiment, a function to merge a contaminant particle/defect detection result detected by the first measurement unit 110 and the contaminant particle/defect detection result detected by the second measurement unit 111 is provided as another function. By using this function, only by means of the secondary scan with the translation stage 104 only for the stroke corresponding to ½ of the maximum inspection radius, substantially the entire region on the semiconductor wafer 100 surface can be inspected, and an inspection throughput can be improved by approximately twice, excluding a set-up time such as replacement time of the semiconductor wafer 100 and the like.

Figure 5:
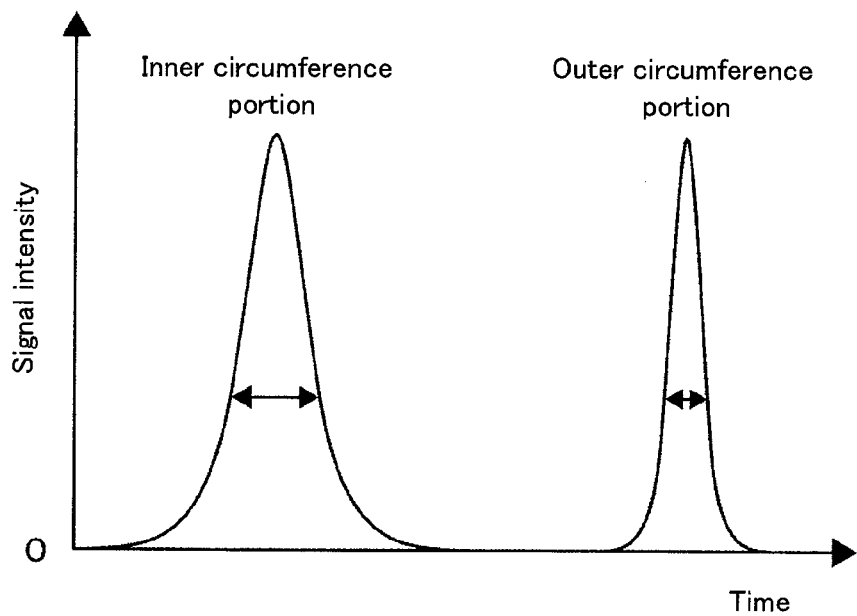
FIG. 5 is a diagram illustrating a difference of signal waveforms between an inner circumference portion and an outer circumference portion.

In this embodiment, substantially in the entire region from the inner circumference to the outer circumference of the semiconductor wafer 100, the rotation stage 103 is driven at a substantially constant angular velocity and the translation stage 104 at a substantially constant linear velocity. As a result, a relative moving linear velocity of the illumination spot 3 with respect to the surface of the semiconductor wafer 100 is larger on the outer circumference portion than on the inner circumference portion. Thus, time during which a contaminant particle on the semiconductor wafer 100 goes across a distance of a short axis d2 of the illumination spot 3 is shorter when the contaminant particle is on the outer circumference portion of the semiconductor wafer 100 than on the inner circumference portion, and thus, as shown in FIG. 5 in general, a time change signal waveform of a scattering light signal obtained from the photodetector 7 via the amplifier 26 has a smaller half-value width of a signal peak if the contaminant particle is located on the outer circumference portion, that is, at a spot with a larger radius in the secondary scan direction. An effective total signal amount of the scattering light signal generated when a single contaminant particle or defect goes across the illumination spot 3 once may be considered to be substantially proportional to an area of the signal peak waveform. On the other hand, in a noise component at detection of the contaminant particle/defect, a shot noise deriving from background scattering light generated from the illuminated illumination spot 3 region on the semiconductor wafer 100 surface is generally predominant, and a light amount of the background scattering light is constant regardless of the linear velocity. Then, if the stage for moving the article to be inspected is driven with a constant size and illuminance of the illumination spot 3 and at a constant primary-scan rotational speed and a constant secondary-scan speed, it can be easily expected that the effective total signal amount is smaller when the same contaminant particle is on the outer circumference portion than on the inner circumference portion on the semiconductor wafer 100, and thus, the signal-to-noise ratio of the signal detection is lowered. It is needless to say that the drop in the effective total signal amount can be prevented by lowering the linear velocity on the outer circumference portion of the stage for moving an article to be inspected, but in that case, it can be also easily expected that the inspection throughput is lowered at the same time.

When a difference between the inner circumference portion and the outer circumference portion of the semiconductor wafer 100 is seen from another viewpoint, if the size and illuminance of the illumination spot 3 are constant, time during which a certain point on the semiconductor wafer 100 goes across the distance of the short axis d2 of the illumination spot 3 becomes shorter on the outer circumference portion where the linear velocity is higher. When seen from a point on the semiconductor wafer 100, it can be easily expected as a natural consequence that the illumination spot of the same illuminance and the same size passes on it in a shorter time, and a total heat amount given by the irradiated beam in the passage time becomes smaller and as a result, temperature rise generated in the periphery of the point also becomes smaller. Actually, the above-mentioned Laser Process Art Handbook indicates that as a calculation result when a heat source is moved, the temperature rise at a specific point is in inverse proportion to the power of ½ of the moving speed of the heat source. If this is considered to the contrary as a problem to keep the temperature rise on the semiconductor wafer 100 surface constant, it is known that in the case of a large light input as on the outer circumference portion, that is, when the size of the illumination spot is constant, the illuminance can be made higher as in the following formula.

Temperature rise∝average illuminance of illumination spot/(power of ½ of linear velocity of heat-source movement) (1)

∴ Under the condition of temperature rise=constant,

Average illuminance of illumination spot/(power of ½ of linear velocity of heat-source movement) =constant (2)

Figure 6:
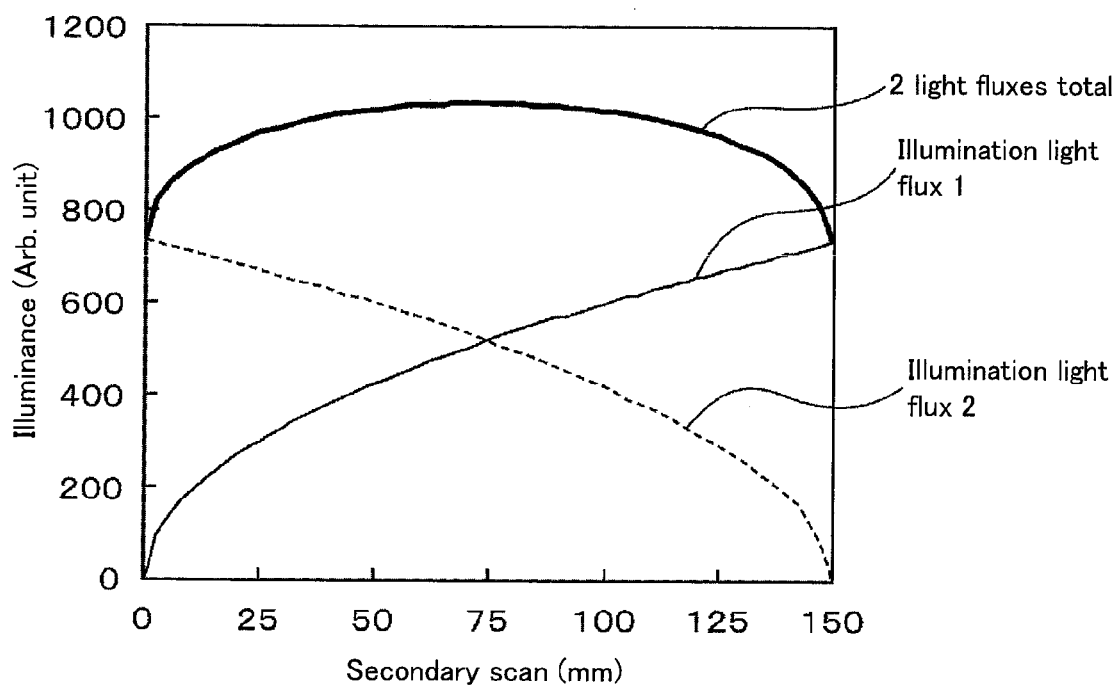
FIG. 6 is a diagram for explaining illuminance control of a measurement spot of the first embodiment.

On the other hand, since it is known that the scattering light intensity from the contaminant particle/defect is in proportion to the illuminance by which the contaminant particle/defect is illuminated, if the illuminance can be made higher as the linear velocity is higher, the effect that the effective total signal amount is lowered if the linear velocity is higher can be compensated, if not perfect. In this embodiment, since the inspection progresses with the two measurement units 110, 111 at the same time, the illuminance control is carried out for the both illumination spots. In this embodiment, as mentioned above, with the secondary scan of the translation stage 104, the first measurement spot moves on the semiconductor wafer 100 surface from the center of the semiconductor wafer 100 to the outer circumference, while the second measurement spot moves from the outer circumference of the semiconductor wafer 100 toward the center to the contrary, and the illuminance of the first measurement spot is controlled in an increasing direction with the progress of the inspection, while the illuminance of the second measurement spot is controlled in a decreasing direction with the progress of the inspection. A state of the illuminance control that should be carried out for the both illumination spots on the basis of the formula (2) is shown in FIG. 6. As can be known from the state of change of the "illuminance of the first measurement spot+illuminance of the second measurement spot" shown in FIG. 6, a change in total of the illuminances of the both spots to the movement of the translation stage 104 is small and substantially flat. Therefore, by controlling a dimming amount at the light-amount adjustment mechanism 40 and the illuminances of the both measurement spots by changing a light amount distribution ratio to the two measurement units at the illumination light-flux dividing optics 41 while keeping the relation of the formula (2), such a merit can also be obtained that an output of the underlying illumination laser light source 11 can be used substantially effectively all the time. Specifically, first, an allowed value Pmax of [average illuminance of illumination spot/(power to ½ of linear velocity of heat-source movement)] in the formula (2) is determined in advance on the basis of the characteristics of the semiconductor wafer 100. And at an actual inspection under a condition of a constant angular velocity, the illuminance control portion 50 acquires a value of the linear velocity from the value of the angular velocity and the secondary scan coordinate value (that is, a radius) for each measurement spot and calculates an allowed illuminance value determined from Pmax and the linear velocity value. Subsequently, the illuminance control portion 50 converts each calculated illuminance value to an illumination light amount to be distributed to each measurement unit. And the portion controls the light-amount adjustment mechanism 40 according to the total value of the distributed light amounts to the both measurement units and controls the illumination light-flux dividing optics 41 according to the ratio of the distributed light amounts to each measurement unit. As a result, the illuminance in the illumination spot 3 can be made larger on the outer circumference portion than on the inner circumference portion, and sensitivity drop caused by the difference in the linear velocities can be compensated, if not perfect. Also, by choosing a value of the maximum output as the illumination laser light source matching the maximum value on the scan radius of the total value of the distributed light amounts to the both measurement units, the light amount disposed of at the light-amount adjustment mechanism 40 can be made minimum, and the output of the illumination laser light source can be used effectively.

As mentioned above, in this embodiment, two measurement units are provided and the inspection results obtained from the two measurement spots are integrated and the light amount distribution of each measurement spot is controlled as above so that the inspection signal-to-noise can be improved or the inspection throughput can be improved, the detection sensitivity difference of the contaminant particle/defect between the inner circumference portion and the outer circumference portion of the semiconductor wafer can be improved, and the output of the mounted illumination laser light source can be effectively used as compared with the contaminant particle/defect inspecting device of the prior art.

Second Embodiment

Figure 7A:
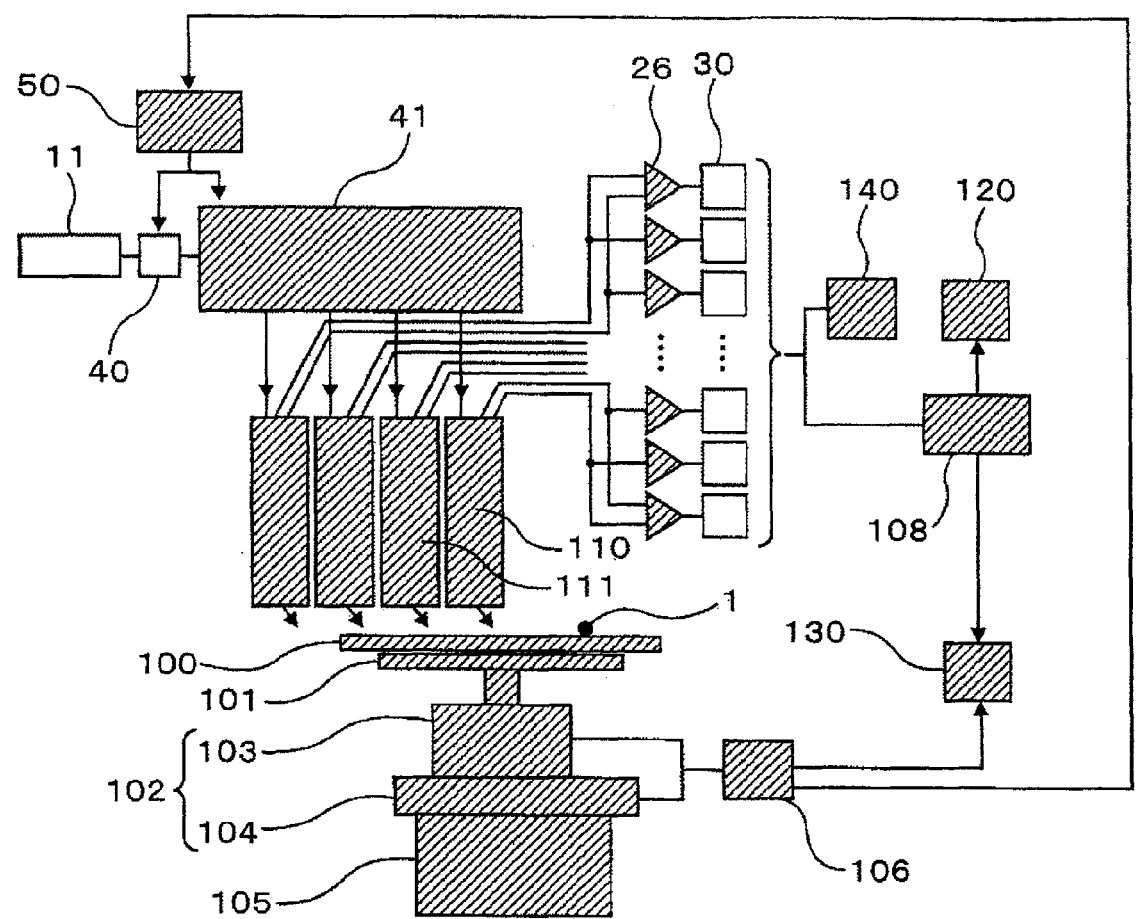
FIGS. 7A and 7B are diagrams illustrating configuration of a second embodiment of the surface inspection apparatus according to the present invention.
Figure 7B:
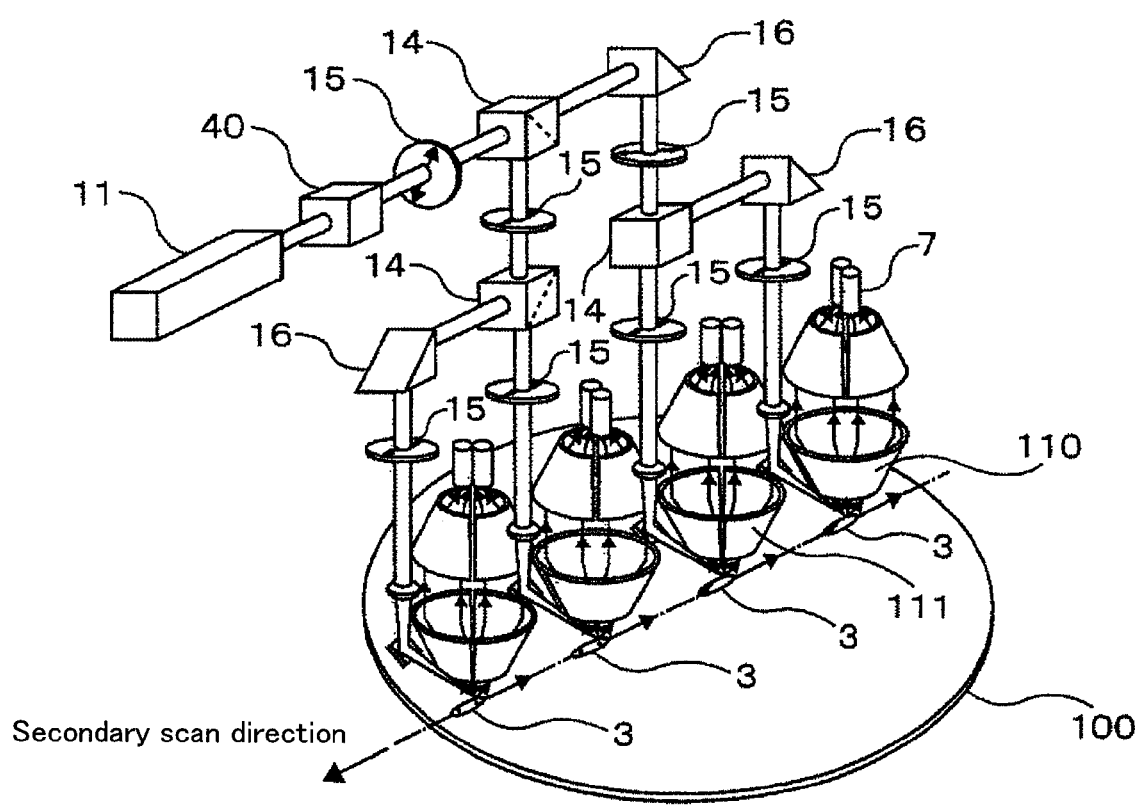
Figure 8:
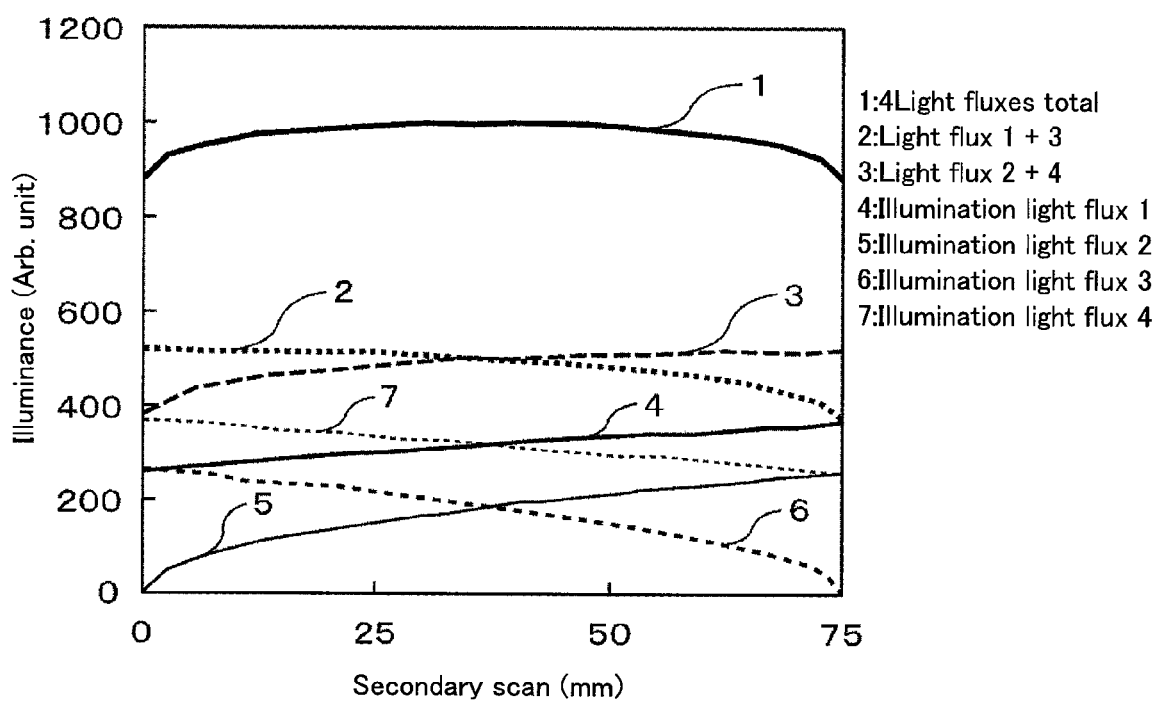
FIG. 8 is a diagram for explaining illuminance control of a measurement spot of the second embodiment.

In the above first embodiment, the number of measurement units for inspecting the semiconductor wafer 100 surface at the concurrent progress is two, but the number can be further increased in installation by reducing an outer dimension of the measurement unit. Configuration in which the number of measurement units is four is shown in FIGS. 7A and 7B as a second embodiment. Moving directions of four first to fourth measurement spots and moving ranges in this embodiment are shown in Table 1. A state of the illuminance control to be carried out for these four illumination spots on the basis of the formula (2) is shown in FIG. 8. A state of change of the "four illuminance total" to the movement of the translation stage 104 shown in FIG. 8 is small similarly to the first embodiment and substantially flat. By carrying out secondary scan with the translation stage 104 only for a stroke corresponding to ½ of the maximum inspection radius with this setting, the second measurement spot and the third measurement spot can both scan an area of ½ of substantially the entire region from the center of the semiconductor wafer 100 to the circumference corresponding to ½ of the maximum inspection radius, and the first measurement spot and the fourth measurement spot can both scan an area of ½ of substantially the entire region from the outer circumference corresponding to the maximum inspection radius of the semiconductor wafer 100 to the circumference corresponding to ½ of the maximum inspection radius, and each point in the entire inspection region on the semiconductor wafer 100 surface is scanned by two measurement spots without fail. From this fact, in this embodiment, by adding the digital data from the two measurement units corresponding to the same coordinate position on the semiconductor wafer 100 surface for use, improvement of the detection signal-to-noise ratio by $\sqrt{2}$ times on an average can be expected as compared with the case where only the digital data from a single measurement unit is used. Also, by providing a function to merge the contaminant particle/defect detection results detected by the four measurement units, by means of the secondary scan with the translation stage 104 only for the stroke corresponding to ½ of the maximum inspection radius, the first measurement spot can inspect substantially the entire region on the semiconductor wafer 100 surface, and an inspection throughput can be improved by approximately twice, excluding a set-up time such as replacement time of the semiconductor wafer 100 and the like. Also, in this embodiment, as mentioned above, since "each point in the entire inspection region on the semiconductor wafer 100 surface is scanned by two measurement spots without fail", in the two measurement units corresponding to the two measurement spots, it is possible to change a detection method of the scattered light. Specifically, one of the measurement units (the second and fourth measurement units, for example) is constituted by providing a collecting concave mirror group for mainly capturing the forward scattering light and a collecting concave mirror group for mainly capturing the backward scattering light, while the other measurement unit (the first and third measurement units, for example) is constituted by providing a collecting concave mirror group for mainly capturing the left side-scattering light and a collecting concave mirror group for mainly capturing the right side-scattering light. As a result, at all the points in the entire inspection region on the semiconductor wafer 100 surface, information on a "ratio between forward scattering light intensity: backward scattering light intensity" and a "ratio between left side-scattering light intensity: right side-scattering light intensity" can be obtained. As a result, it is needless to say that accuracy of determining a type of a contaminant particle/defect is improved. Since the other configurations, controls, effects are the same as those in the first embodiment, detailed description will be omitted.

Third Embodiment

Figure 9A:
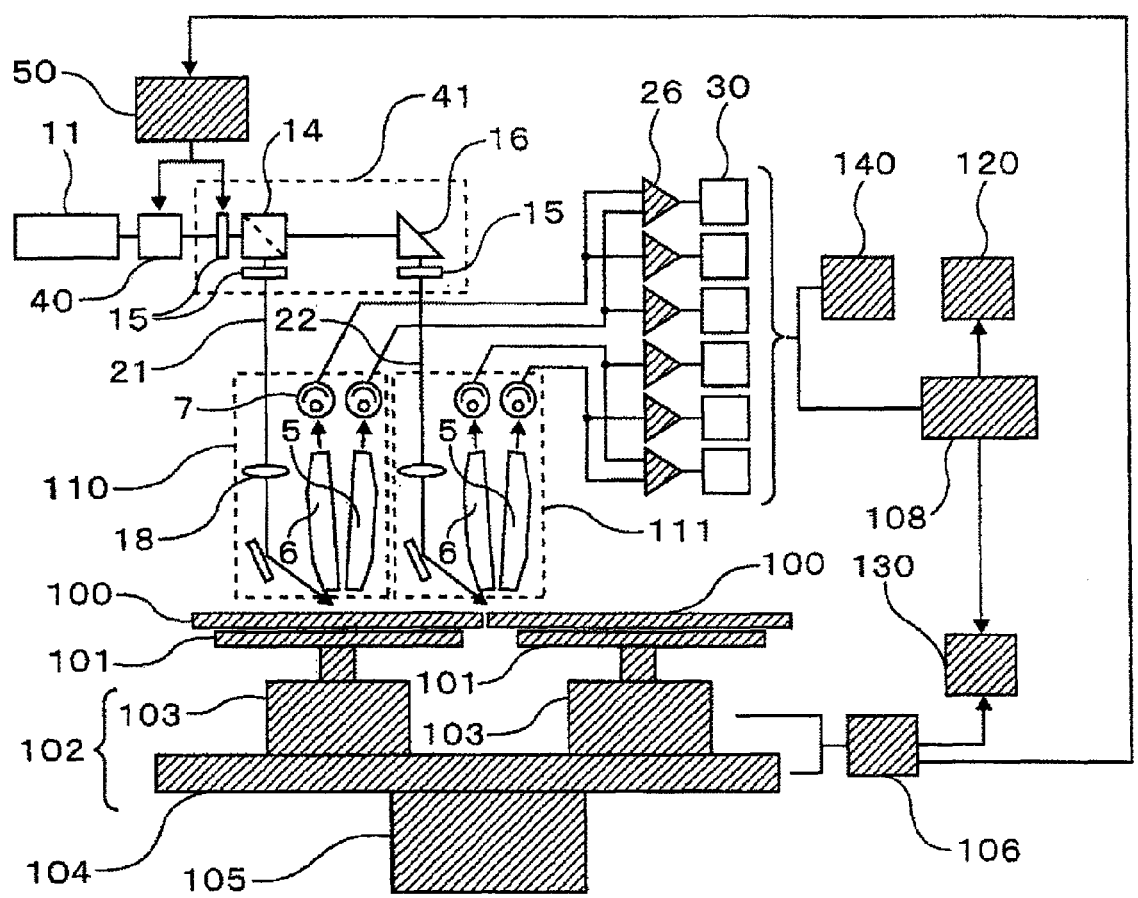
FIGS. 9A and 9B are diagrams illustrating configuration of a third embodiment of the surface inspection apparatus according to the present invention.
Figure 9B:
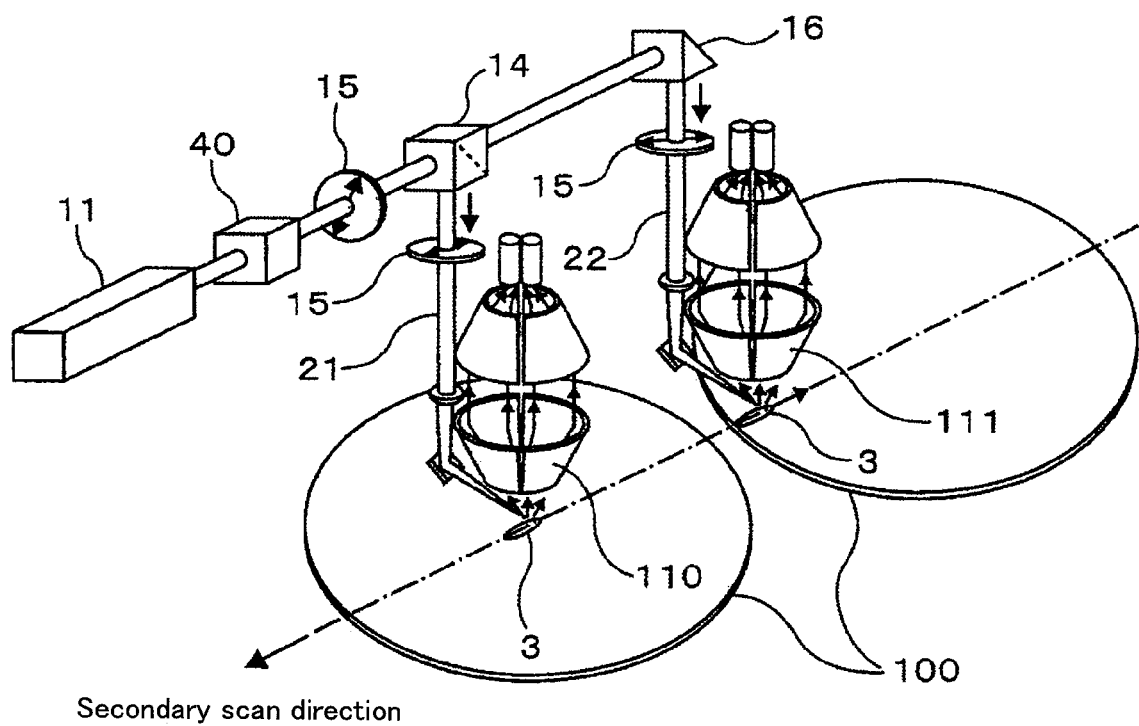

In the first and second embodiments, the configuration in which a single semiconductor wafer is inspected by a plurality of measurement units at the same time is shown, but it is possible to configure that a surface inspection apparatus can inspect two semiconductor wafers concurrently and two measurement units are provided so that each semiconductor wafer is inspected by each of the measurement units. This configuration is shown in FIGS. 9A and 9B as a third embodiment. In order to inspect two semiconductor wafers concurrently, it is only necessary that a combination of the translation stage 104, the rotation stage 103, and the Z stage 105 is provided at each semiconductor wafer or two units <combination of the rotation stage 103 and the Z stage 105> are mounted on the common single translation stage 104. In FIGS. 9A and 9B, the latter configuration in which the translation stage is made common is shown. By carrying out the secondary scan with the translation stage 104 only for a stroke corresponding to the maximum inspection radius in this embodiment, each measurement spot of the two measurement units can scan substantially the entire region from the center of each semiconductor wafer 100 to the outer circumference corresponding to the maximum inspection radius, and a point in the entire inspection region on the two semiconductor wafer 100 surface is scanned by a single measurement spot without a fail. By means of the secondary scan with the translation stage 104 only for a stroke corresponding to the maximum inspection radius once, substantially the entire region on the two semiconductor wafer 100 surfaces can be inspected, and an inspection throughput can be improved by approximately twice, excluding a set-up time such as replacement time of the semiconductor wafer 100 and the like. The distribution control of the illumination light amounts to the two measurement units is the same as in the first embodiment.

What is claimed is:

1. A surface apparatus comprising:
a stage for moving an article to be inspected with primary scan of rotational movement and secondary scan of translational movement, on which an article to be inspected is mounted;
an illumination optics for forming an illumination spot by irradiating an illumination light flux from a light source to a predetermined position on the surface of the article to be inspected mounted on the stage for moving an article to be inspected;
a collection optics for collecting light scattered, diffracted or reflected from the illumination spot; and
a light detection optics for detecting the scattered light, diffracted light or reflected light collected by the collection optics and converting it to an electric signal, wherein
a plurality of measurement units including the illumination optics, the collection optics, and the light detection optics are arranged substantially along the secondary scan direction of the stage for moving an article to be inspected; and
wherein the stage for moving an article to be inspected moves/scans the article to be inspected at linear velocities different between an inner circumference portion of the article to be inspected and an outer circumference portion of the article to be inspected by combination of the primary scan and the secondary scan, and on the basis of information from the plurality of measurement units, a contaminant particle or a defect present on the surface or in the vicinity of the surface of the article to be inspected is detected.

2. The surface inspection apparatus according to claim 1, wherein
at least one of the plurality of illumination spots irradiated by the plurality of measurement units is configured to be moved toward the inner circumference portion of the surface of the article to be inspected during the secondary scan, and another at least one of the illumination spots is moved toward the outer circumference portion.

3. The surface inspection apparatus according to claim 2, wherein
the plurality of measurement units is configured to be able to illuminate the surface of the article to be inspected with different illuminances.

4. The surface inspection apparatus according to claim 3, wherein
the illuminance of each illumination spot of the plurality of measurement units is configured to be able to be changed during the secondary scan.

5. The surface inspection apparatus according to claim 4, wherein
the illuminance of each illumination spot of the plurality of measurement units is configured to be changed corresponding to a radial position of each illumination spot on the surface of the article to be inspected so that the illuminance becomes low as the position goes toward the inner circumference portion on the surface of the article to be inspected, while it becomes high toward the outer circumference portion.

6. The surface inspection apparatus according to claim 5, wherein
at least one or more measurement units in the plurality of measurement units comprise a collection optics for collecting scattered/diffracted/reflected light from an illumination spot by two or more plural azimuthal directions and a light detection optics made of a plurality of photodetectors for individually detecting the scattered/diffracted/reflected light collected by the plurality of azimuthal directions and converting it to an electric signal or one photodetector having a plurality of photosensitive pixels.

7. The surface inspection apparatus according to claim 5, wherein
at least two or more of the plurality of measurement units are arranged so that inspection regions to be filled by traces drawn by the illumination spot on the surface of the article to be inspected with the primary scan rotation and secondary scan movement of the stage for moving the article to be inspected substantially overlap each other, and an inspection result of the overlapped inspection regions is configured to obtain the inspection results of each of the measurement units in integration.

8. The surface inspection apparatus according to claim 6, wherein
one of the measurement unit pair whose inspection regions substantially overlap each other has the collection optics for mainly collecting forward scattering light and backward scattering light individually in the light scattered from the illumination spot and a light detection optics including two photodetectors for individually detecting the focused forward scattering light and backward scattering light and converting them to electric signals or one photodetector having two photosensitive pixels;
while the other measurement unit is provided with the collection optics for mainly collecting right side-scattering light and left side-scattering light individually in the light scattered from the illumination spot and a light detection optics including two photodetectors for individually detecting the focused right side-scattering light and left side-scattering light and converting them to electric signals or one photodetector having two photosensitive pixels.

9. A surface inspection apparatus comprising:
a stage for moving an article to be inspected with primary scan of rotational movement and secondary scan of translational movement, on which an article to be inspected is mounted;

an illumination light-flux dividing optics for dividing a light flux emitted from a light source into plural;
an illumination optics for forming an illumination spot by irradiating one of the illumination light fluxes divided by the illumination light-flux dividing optics to a predetermined position on the surface of the article to be inspected;
a collection optics for collecting light scattered, diffracted or reflected from the illumination spot;
a light detection optics for detecting the scattered light, diffracted light or reflected light collected by the collection optics and converting it to an electric signal; and
a plurality of measurement units including the illumination optics, the collection optics and the light detection optics, wherein
the plurality of measurement units are arranged substantially along the secondary scan direction of the stage for moving an article to be inspected.

10. The surface inspection apparatus according to claim 9, wherein
an illuminance in the illumination spot is controlled on the basis of a linear velocity determined by combination of a rotation speed (primary scan speed) and a translation speed (secondary scan speed) of the stage for moving an article to be inspected.

11. The surface inspection apparatus according to claim 9, wherein
the illuminance in the illumination spot is controlled on the basis of secondary scan coordinate information of the stage for moving an article to be inspected.

12. The surface inspection apparatus according to claim 9, wherein
at least one illumination spot of the plurality of illumination spots irradiated onto the surface of the article to be inspected by the plurality of measurement units is configured to be moved on the surface of the article to be inspected toward an inner circumference portion during the secondary scan; and
another at least one illumination spot is moved toward an outer circumference portion.

13. The surface inspection apparatus according to claim 12, wherein
the plurality of measurement units are configured to be able to illuminate the surface of the article to be inspected with different illuminances.

14. The surface inspection apparatus according to claim 13, wherein
an illuminance of each illumination spot included in the plurality of measurement units is configured to be changed during the secondary scan.

15. The surface inspection apparatus according to claim 14, wherein
a mechanism for changing the illuminance for illuminating the surface of the article to be inspected by the illumination light-flux dividing optics is a mechanism for changing an intensity ratio of two light fluxes separated by a polarization separation element by combining the polarization separation element such as a polarization beam splitter, Wollaston prism and the like and a half-wave plate and by changing a direction of a slow axis of the half-wave plate with respect to a polarization azimuth of the polarization separation element through rotation.

16. The surface inspection apparatus according to claim 14, wherein
the illuminance of each illumination spot included in the plurality of measurement units is configured to be changed corresponding to a radial position of each illumination spot on the surface of the article to be inspected so that the illuminance becomes low as the position goes toward the inner circumference portion on the surface of the article to be inspected, while it becomes high toward the outer circumference portion.

17. The surface inspection apparatus according to claim 16, wherein
the collection optics uses a concave mirror as a collection optical element.

18. The surface inspection apparatus according to claim 16, wherein
at least one or more measurement units in the plurality of measurement units comprise a collection optics for collecting scattered/diffracted/reflected light from an illumination spot by two or more plural azimuthal directions and a light detection optics made of a plurality of photodetectors for individually detecting the scattered/diffracted/reflected light focused by the plurality of azimuthal directions and converting it to an electric signal or one photodetector having a plurality of photosensitive pixels.

19. The surface inspection apparatus according to claim 16, wherein
at least two or more of the plurality of measurement units are arranged so that inspection regions to be filled by traces drawn by the illumination spot on the surface of the article to be inspected with the primary scan rotation and secondary scan movement of the stage for moving the article to be inspected substantially overlap each other, and an inspection result of the overlapped inspection regions is configured to obtain the inspection results of each of the measurement units in integration.

20. The surface inspection apparatus according to claim 19, wherein
one of the measurement unit pair whose inspection regions substantially overlap each other has the collection optics for mainly collecting forward scattering light and backward scattering light individually in the light scattered from the illumination spot and a light detection optics including two photodetectors for individually detecting the focused forward scattering light and backward scattering light and converting them to electric signals or one photodetector having two photosensitive pixels;
while the other measurement unit is provided with the collection optics for mainly collecting right side-scattering light and left side-scattering light individually in the light scattered from the illumination spot and a light detection optics including two photodetectors for individually detecting the focused right side-scattering light and left side-scattering light and converting them to electric signals or one photodetector having two photosensitive pixels.

21. The surface inspection apparatus according to claim 18, wherein
the measurement unit is provided with a collection optics for individually collecting substantially forward scattering light, substantially backward scattering light, substantially left side-scattering light, and substantially right side-scattering light, and a light detection optics made of four photodetectors for individually detecting the substantially forward scattering light, the substantially backward scattering light, the substantially left side-scattering light, and the substantially right side-scattering light above collected and converting them to electric signals or one photodetector having four photosensitive pixels.

22. A surface inspection apparatus comprising:
- a stage for moving an article to be inspected with primary scan of rotational movement and secondary scan of translational movement, on which an article to be inspected is mounted;
- an illumination light-flux dividing optics for dividing a light flux emitted from a light source into plural;
- an illumination optics for forming an illumination spot by irradiating one of the illumination light fluxes divided by the illumination light-flux dividing optics into plural to a predetermined position on the surface of the article to be inspected;
- a collection optics for collecting light scattered, diffracted or reflected from the illumination spot;
- a light detection optics for detecting the scattered light, diffracted light or reflected light collected by the collection optics and converting it to an electric signal; and
- two measurement units including the illumination optics, the collection optics, and the light detection optics, in which
- two units of the stage for moving an article to be inspected or two units of primary scan mechanism are mounted on a common secondary scan mechanism so that two articles to be inspected can be inspected substantially at the same time; and
- by combination of the primary scan and secondary scan, while the article to be inspected is moved/scanned at linear velocities different between its inner circumference portion and an outer circumference portion, a contaminant particle or a defect present on the surface of the article to be inspected or inside the vicinity of the surface is detected by detecting scattered light, diffracted light or reflected light from the illumination spot formed by irradiation onto a predetermined position on the surface of the article to be inspected, wherein
- the two measurement units are made to correspond to the two articles to be inspected mounted on the primary scan mechanism of the two units of the stage for moving an article to be inspected or two primary scan mechanisms having the common secondary scan mechanism;
- wherein the two measurement units are arranged substantially along the secondary scan direction of the stage for moving an article to be inspected.

23. The surface inspection apparatus according to claim 22, wherein
in two illumination spots irradiated to the two articles to be inspected from the two measurement units, one illumination spot is moved on the surface of the corresponding article to be inspected toward the inner circumference portion during the secondary scan, while the other illumination spot is moved on the surface of the corresponding article to be inspected toward the outer circumference portion during the secondary scan.

24. The surface inspection apparatus according to claim 23, wherein
the surface of the article to be inspected is configured to be able to be illuminated by the two measurement units with different illuminances.

25. The surface inspection apparatus according to claim 24, wherein
the illuminance of each illumination spot of the two measurement units is configured to be changed during movement of the secondary scan.

26. The surface inspection apparatus according to claim 25, wherein
a mechanism for changing the illuminance for illuminating the surface of the article to be inspected by the illumination light-flux dividing optics is a mechanism for changing an intensity ratio of two light fluxes separated by a polarization separation element by combining the polarization separation element such as a polarization beam splitter, Wollaston prism and the like and a half-wave plate and by changing a direction of a slow axis of the half-wave plate with respect to a polarization azimuth of the polarization separation element through rotation.

27. The surface inspection apparatus according to claim 25, wherein
the illuminance of each illumination spot of the two measurement units is configured to be changed corresponding to a radial position of each illumination spot on the surface of the corresponding article to be inspected so that the illuminance becomes low as the position goes toward the inner circumference portion on the surface of the article to be inspected, while it becomes high toward the outer circumference portion.

* * * * *